(12) United States Patent
Martinsen et al.

(10) Patent No.: US 8,565,850 B2
(45) Date of Patent: Oct. 22, 2013

(54) METHOD AND KIT FOR SWEAT ACTIVITY MEASUREMENT

(75) Inventors: Ørjan Grøttem Martinsen, Stabekk (NO); Sverre Jøran Grimnes, Oslo (NO); Erik Fosse, Oslo (NO)

(73) Assignee: Universitetet i Oslo, Oslo (NO)

( * ) Notice: Subject to any disclaimer, the term of this patent is extended or adjusted under 35 U.S.C. 154(b) by 813 days.

(21) Appl. No.: 12/666,050

(22) PCT Filed: Jul. 1, 2008

(86) PCT No.: PCT/EP2008/058437
§ 371 (c)(1),
(2), (4) Date: Dec. 22, 2009

(87) PCT Pub. No.: WO2009/004001
PCT Pub. Date: Jan. 8, 2009

(65) Prior Publication Data
US 2010/0179403 A1    Jul. 15, 2010

Related U.S. Application Data

(60) Provisional application No. 60/947,547, filed on Jul. 2, 2007.

(51) Int. Cl.
*A61B 5/05* (2006.01)

(52) U.S. Cl.
USPC .................................... 600/346; 600/306

(58) Field of Classification Search
USPC ................... 600/300, 301, 306, 345–346
See application file for complete search history.

(56) References Cited

U.S. PATENT DOCUMENTS 5,738,107 A * 4/1998 Martinsen et al. ............ 600/547
5,957,854 A * 9/1999 Besson et al. ................ 600/509

(Continued)

FOREIGN PATENT DOCUMENTS

EP    0315854 A1    5/1989
JP    07303618 A    11/1995

(Continued)

OTHER PUBLICATIONS

Jossinet et al., "Hydrogel electrodes in biosignal recording," 1990, *Annual International Conference of the IEEE Engineering in Medicine and Biology Society* 12(4):1490-1491.
Lackermeier et al., "In vivo ac impedance spectroscopy of human skin," 1999, *Ann. N. Y. Acad. Sci.* 873:197-213.
Martinsen et al., "An instrument for the evaluation of skin hydration by electrical admittance measurements," 1993, *Innov. Tech. Biol. Med.* 14(5):589-596.

(Continued)

*Primary Examiner* — Patricia Mallari
*Assistant Examiner* — Michael D'Angelo
(74) *Attorney, Agent, or Firm* — Knobbe Martens Olson & Bear LLP

(57) ABSTRACT

The invention relates to sweat activity measurement, e.g. for determining a physiological state of a subject, embodied by a method as well as a kit with an immittance measuring circuit and electrodes with contact electrolyte. Sweat activity is considered a transport phenomenon and can be defined as a flux, e.g. gram water per skin area per second. Prior art methods determining water absorbed per gram dry stratum corneum measures skin moisture and do not truly reflect sweat activity. A periodic signal with frequency of 60 Hz or lower is applied to reduce contribution from complex admittance of the skin, and skin conductance is measured as a degree of sweat activity. The contact electrolyte allows filling of sweat ducts with sweat from sweat glands, this may be characterized in that it does not substantially fill the sweat ducts when being positioned on the skin and/or in that it has a re-absorption time constant from the sweat ducts into the Epidermis of less than 15 min.

15 Claims, 5 Drawing Sheets

(56) References Cited

U.S. PATENT DOCUMENTS 6,032,060 A 2/2000 Carim et al.
7,052,472 B1 * 5/2006 Miller et al. .................. 600/549

FOREIGN PATENT DOCUMENTS

| JP | 2005052227 A | 3/2005 |
| WO | WO 92/06634 | 4/1992 |
| WO | WO 96/10951 | 4/1996 |
| WO | WO 2004/049937 A1 | 6/2004 |

OTHER PUBLICATIONS

McAdams et al., "AC impedance of the hydrogel-skin interface," 1994, *Annual Conference of the IEEE Engineering in Medicine and Biology Society* 2:870-871.

Mørkrid, "Continuous estimation of parameters in skin electrical admittance at two different frequencies," 1988, *Med. & Biol. Eng. & Comput.* 26:633-640.

Shamsuddin, "Continuous monitoring of sweating by electrical conductivity measurement," 1998, *Physiol. Meas.* 19:375-382.

* cited by examiner

METHOD AND KIT FOR SWEAT ACTIVITY MEASUREMENT

CROSS REFERENCE TO RELATED APPLICATIONS

This application claims the benefit and priority to and is a U.S. National Phase Application of PCT International Application Number PCT/EP2008/058437, filed on Jul. 1, 2008, designating the United States of America and published in the English language, which is an International Application of and claims the benefit of priority to U.S. Provisional Application No. 60/947,547, filed on Jul. 2, 2007. The disclosures of the above-referenced applications are hereby expressly incorporated by reference in their entireties.

FIELD OF THE INVENTION

The present invention is related to sweat measurement. More particularly the present invention is related to a method for determining a physiological state of a subject by registering sweat activity and a kit of parts for enabling the execution of the method.

BACKGROUND OF THE INVENTION

Sweating in a human is to a large extent controlled from the hypothalamus through autonomic pathways and the sympathetic nervous system to the skin everywhere in the body. It is thus a very central regulation, and large synchrony between different skin sites is to be expected. The main purposes of sweating are for the a) thermal balance of the body, b) obtaining best frictional properties of hands and feet, c) psychosomatic functions related to e.g. nervousness ("cold" sweating), gustatory sweating during eating or sweating correlated to face flushing.

Some persons have problems with too little or too strong sweating, locally or affecting larger parts of the body. The situation of too much sweating may be so serious that it is classified as a disease: hyperhidrosis. Four classes of therapy are used: treatment with aluminium salts, dc current through the affected skin area, sympatectomi and injection of botulintoxin. As the last two methods are invasive, and as many patients are not satisfied with their therapy, there is an ongoing search for reliable diagnostic methods and tools. Up to now simple and robust ambulatory measurements of sweat activity on several skin sites simultaneously have not been possible.

In the prior art several solutions for measuring skin moisture (i.e. hydration, water content, dryness) by utilizing skin impedance measurements are known.

U.S. Pat. No. 5,738,107 describes the measurement of skin moisture by an electrical susceptance method and the use of at least two sensors (electrodes).

European patent application EP 0 315 854 A1 describes the measurement of skin moisture in the keratinous layer (=stratum corneum) by measuring impedance. The measurements are switched so that both the surface and the depth of the keratinous layer can be measured.

International Patent Publication WO 92/06634 describes depth selective, localized measurements of electric impedance in organic and biological materials. The depth selectivity is obtained by inserting an actively driven third electrode between two measuring electrodes.

Japanese Patent Abstract JP 2005052227 A relates to an instrument measuring the water content in the stratum corneum, Another Japanese Patent Abstract JP 07303618 A relates to an apparatus for the measurement of skin impedance.

In the article "*An instrument for the evaluation of skin hydration by electrical admittance measurement*", by Ø. G. Martinsen & al, in Innov. Tech Biol. Med., Vol. 14, No. 5, 1993, p. 589-596 and in the article "*Continuous estimation of parameters in skin electrical admittance from simultaneous measurements at two frequencies*", by L. Mørkrid and Z.-G. Qiao, in Medical & Biological Engineering & Computing, November 1988, pp. 633-640, there are described electrical impedance measurement at frequencies ranging from 60 Hz to 1 kHz, and in the range 1-1000 kHz, respectively.

The publication "*Continuous monitoring of sweating by electrical conductivity measurement*" by A. K. M. Shamsuddin and T. Togawa, in Physiol. Meas., Vol 19, 1998, pp 375-382, describes a method of measuring changes in the conductivity of perfusing water using a chamber attached to the skin surface. This device requires a source of an ion-free solution and an arrangement of channels for guiding the solution past the skin surface, a solution which is not very attractive for ambulatory use.

SUMMARY OF THE INVENTION

Although it is well known that the stratum corneum (the outer layer of the skin) is a poor electric conductor and that impedance measurements may be used to obtain a measure of water, electrolyte or sweat content in the skin, present techniques for skin impedance measurement either use equipment of a fairly large size and hence cumbersome or impractical for use in ambulatory measurements or they are unable to provide a reliable measurement of the sweat activity in an easy manner.

Hence an improved technique for measuring sweat activity would be advantageous, and in particular a more simple and robust device for performing measurements of sweat activity on several skin sites in a more reliable manner and associated equipment which is suitable for ambulatory use would be highly desirable.

Accordingly, the present invention provides a kit which is suitable for performing measurements of sweat activity in a manner which is in improvement in relation to the abovementioned limitations of known solutions.

In contrast with the prior art techniques briefly summarised above, the present invention is not aimed at measuring moisture content, but rather sweat activity.

The difference between skin moisture and sweat activity may be illustrated be the following example. When the air is cold and dry (winter, low relative humidity) the water transport is high through the stratum corneum (by diffusion) but low through the sweat ducts (low sweat activity), and the skin moisture at the skin surface is low. When the air is warm and dry (desert climate, low relative humidity) the skin surface moisture is also low because of quick evaporation, but the sweat activity is high.

The present invention for sweat activity measurement obtains a measure for the degree of sweat duct filling. Sweat activity is a flux and may be given as for instance gram water per skin area per second [$g/m^2s$], whereas skin moisture is water absorbed per gram dry stratum corneum [dimensionless]. Sweat activity as referred to in this description is a transport phenomenon, while skin moisture is a storage phenomenon.

Even though the prior art in the field is indirectly related to sweat activity via the processes of delayed absorption and desorption processes in the stratum corneum, the prior art solution do not provide measurements of sweat activity directly.

Since sweat activity measurement is a measure of sweat duct volume filling, it is important that the measurement itself does not interfere too much with the filling of the sweat ducts. This happens for example if contact electrolyte from the electrode that penetrates the stratum corneum and fully or partly fills the sweat ducts, is not reabsorbed fast enough into the Epidermis to allow the sweat gland to fill the sweat ducts. Such long-term filling with contact electrolyte would tamper the measurement as the sweat flux from the gland meets a duct already filled with contact electrolyte. With no reabsorption, the ducts will always be filled with either sweat and/or contact electrolyte. The inventors have realised this effect and discovered that the prior art measurement methods have not taken this into account.

Therefore, the objective of the present invention is in one aspect achieved by providing a kit for monitoring sweat activity. The kit comprises an electronic processing unit for measuring a conductance signal and a set of three electrodes to be positioned on skin sites or a body part of a subject. The electrodes are supplied with contact electrolyte for providing electrical contact between the electrodes and the skin sites, the contact electrolyte being characterized in that it allows, i.e. does not hinder or substantially prevent, filling of sweat ducts with sweat from sweat glands over the course of the monitoring when being positioned on the skin sites. The electronic processing unit has an electrode drive circuit for applying a periodic signal with a predetermined frequency of less than 60 Hz, such as preferably less than 45 Hz or less than 30 Hz to at least a first of the electrode to reduce the contribution from the stratum corneum complex admittance and an immittance measuring circuit for measuring at least a conductance signal received from at least a second of the electrodes.

According to the invention, the contact electrolyte allows filling of sweat ducts with sweat from sweat glands because it either does not fill the sweat ducts to a substantial degree, or because it is absorbed into the Epidermis fast enough to allow free filling of the duct at the next expulsion of the sweat gland. Thus, in an alternative formulation the contact electrolyte may be characterized in that it does not fill the sweat ducts to a degree which interferes with the sweat activity to be monitored. In yet another alternative formulation, it may be characterized in that it does not substantially fill the sweat ducts when being positioned on the skin and/or in that it has a re-absorption time constant from the sweat ducts into the Epidermis of less than 15 min., such as preferably less than 10 min.; 8 min.; 5 min.; 3 min.; or 2 min., in the selected skin site. In a preferred embodiment, the contact electrolyte has the property of not penetrating the sweat ducts when being positioned on the skin.

Detailed definition of, and methods for determining, the re-absorption time constant of contact electrolyte from the sweat ducts into the Epidermis will be given elsewhere in the description.

The objective of the invention is in a second aspect of the invention achieved by providing a method for determining a physiological state of a subject by registering sweat activity caused by the sympathetic nervous system. In the method the kit according to the first aspect of the invention is applied.

The object of the invention is in a third aspect of the invention achieved by providing a method for monitoring sweat activity of a subject over time in which there is provided an electronic processing unit for measuring a conductance signal and a set of three electrodes to be positioned on selected skin sites or a body part of a subject. The electrodes are arranged in electric contact with the skin via a contact electrolyte having the property of allowing filling and emptying of sweat ducts with sweat from sweat glands in the skin sites over the course of the monitoring. A periodic signal is applied with a predetermined frequency of less than 60 Hz, such as preferably less than 45 Hz or less than 30 Hz to the electrodes to reduce the contribution from the stratum corneum complex admittance. At least a conductance signal is measured from the signals received from electrodes.

The amount of sweat differs between different skin sites of the body and which site is most active also depends on which is the present main purpose of sweating. Furthermore, the re-absorption (and thus the time constant) of contact electrolyte differs between different skin sites. Therefore, depending on the applications, it may be preferred that the determination of sweat activity or physical state according to the various aspects and embodiments comprises placing the electrodes on specific skin sites related to the purpose of the determination, and preferably to measure on several skin sites simultaneously.

The preferred skin sites may be the extremities including hands and feet, axillaries, thorax and abdomen.

Further preferable embodiments of the kit and the method according to the invention are given in the dependent claims.

THE DRAWINGS

A detailed description of the invention will be made below by reference to the appended drawings in which FIG. 1 illustrates schematically a sweat gland releasing sweat into a sweat duct in the skin.

DETAILED DESCRIPTION OF THE INVENTION

The present inventors have realized that a reliable estimate of sweat activity can be obtained by providing a measure of the degree of filling of the sweat ducts in the skin. In order to explain the invention a short description of the electrical characteristics of the skin is included.

Figure 1:
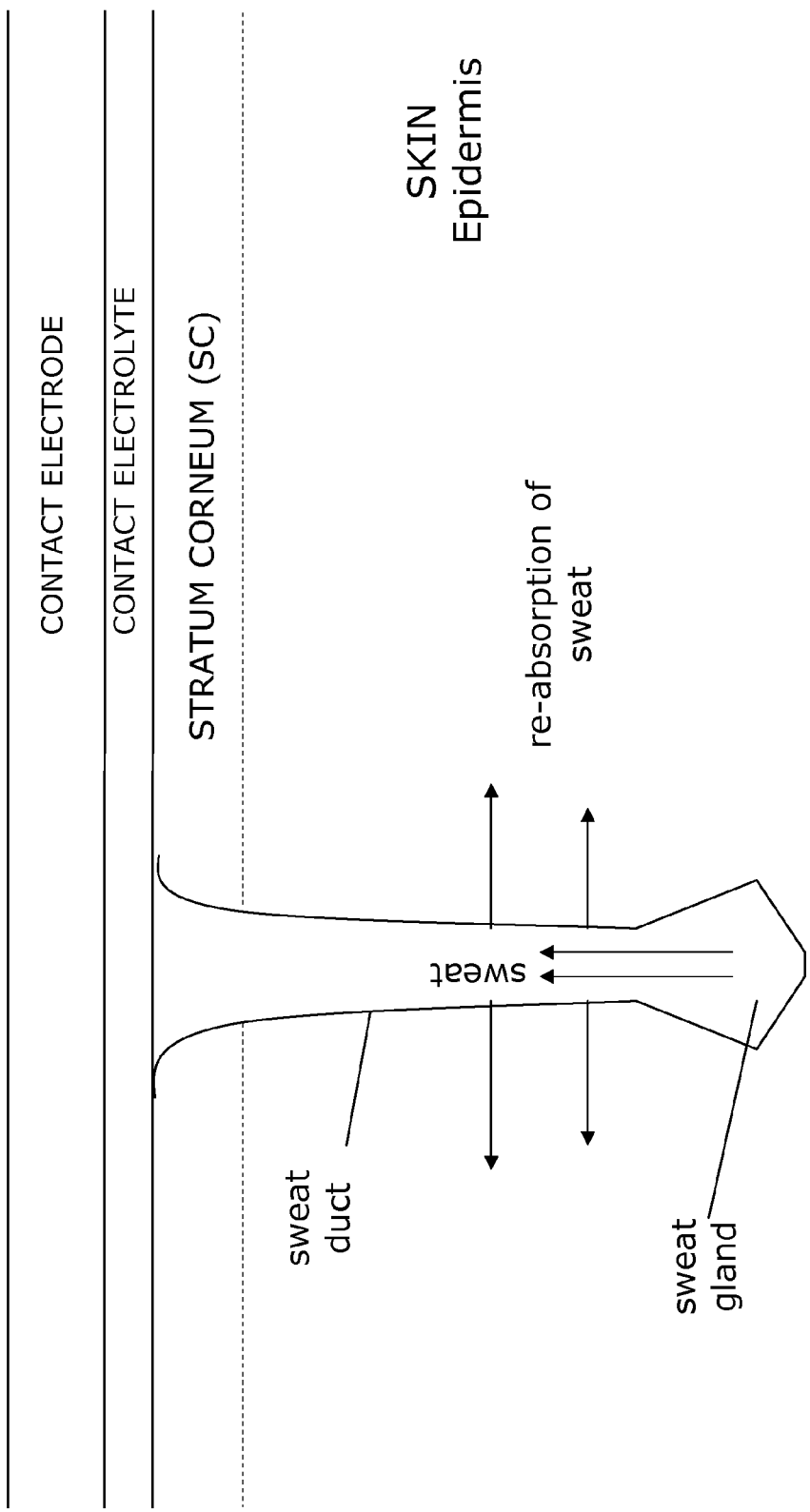

The skin may be electrically modelled as a poorly conducting stratum corneum layer (SC) shunted by sweat ducts containing a variable amount of well conducting sweat, as illustrated schematically on FIG. 1.

Each sweat gland and sweat duct has its individual expulsion and re-absorption time scale and an individual refractory period. The average filling of some hundreds of similar sweat ducts is a measure of the sweat activity. All the ducts will never be completely filled, so that there will be no absolute saturation at high sweat activities.

The filling of a sweat duct represents a conductance increase, but once filled the conductance no longer represents a sweat flow process. The present invention is based on the fact that the sweat ducts empty themselves by a re-absorption process through the duct walls into the surrounding epidermis layers. A sweat gland has a refractory period after expelling sweat. During that period the duct emptying has started, so that a new expulsion does not occur with a filled duct. In that way the sweat activity is most strongly correlated with every increase in ac conductance, but not with the falling part of the conductance curve.

Figure 2:
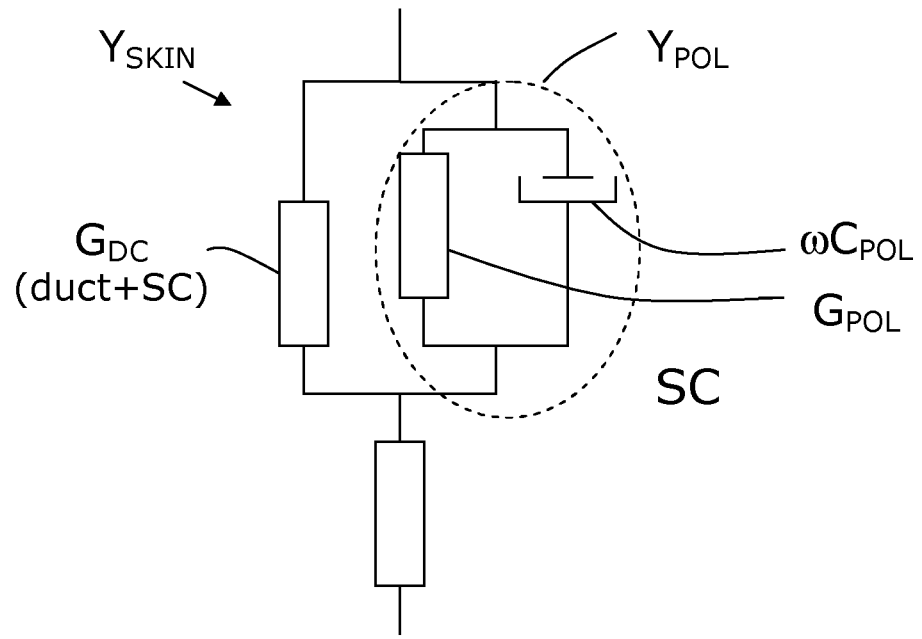
FIG. 2 is an electrical equivalent model of the skin used in the present invention

The sweat ducts in parallel with the stratum corneum are electrically shunting the stratum corneum because they contain electrolytes, mainly $Na^+$ and $CL^-$. As illustrated by FIG. 2, the frequency independent ac conductivity at low frequencies, $G_{DC}$, is related to the degree of filling of the sweat ducts, hence a parameter of focus in the present invention.

Figure 3:
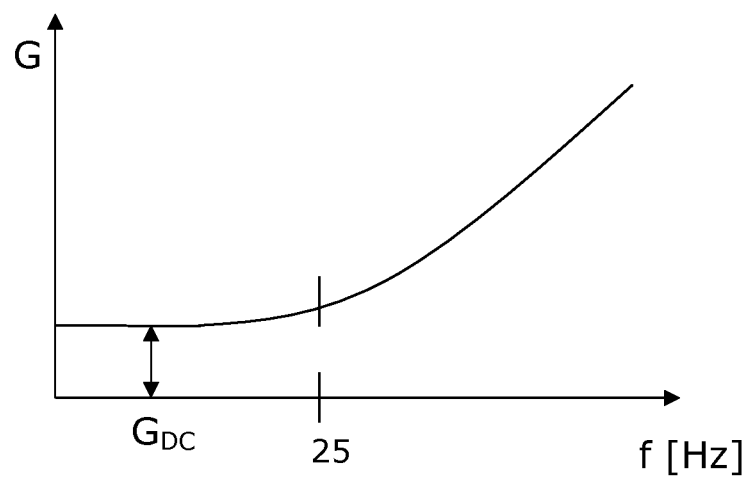
FIG. 3 shows a characteristic curve obtained with a conductance measurement on the skin of a human being.

In addition to the conductance part the complex admittance, the skin has a susceptance component, $\omega C_{POL}$, as shown on FIG. 2. The susceptance is the capacitive part linked with the water absorption in the stratum corneum, which may be considered as an error in the sweat activity measurement of the present invention. The susceptance may be measured separately by extracting the capacitive part, $\omega C_{POL}$ from the complex admittance, Y. The stratum corneum conductivity is exponentially dependent on stratum corneum water content, and can be divided in two components; the first being the dc conductivity, $G_{DC}$, which is the frequency independent conductance measured with a sufficiently low frequency signal (due to electrolytic channels with free water), the second part being the frequency dependent ac conductivity, $G_{POL}$, due to the dielectric losses of the water bound to the polar lipids of the stratum corneum. The ac conductance of the bound water can be made as small as wanted, as illustrated by FIG. 3, by lowering the measuring frequency, and it can therefore also be made insignificant as a source of error. Lowering the frequency to below 30 Hz, say 10 or 25 Hz, the conductance will be dominated by the frequency independent conductance, $G_{DC}$. A lower frequency limit is determined by the required response time, that is, the time from electrode skin contact to stable readout. If for example an answer is wanted within one second the lower frequency limit will be about 3 Hz.

Figure 4:
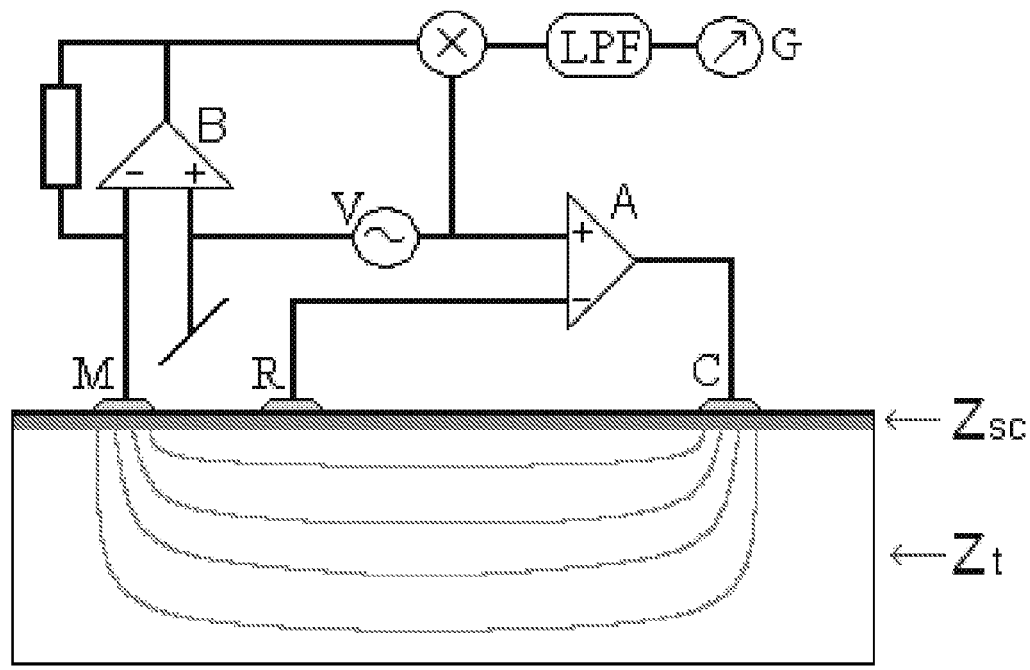
FIG. 4 shows a three-electrode system for performing a measurement of skin tissue conductance according to the invention.

FIG. 4 shows a basic kit according to the invention for monitoring sweat activity. The kit comprises an electronic processing unit comprising first and second operational amplifiers A, B a negative feedback impedance R on the second op.amp. B, a signal multiplier X, a low pass filter LPF, and a conductance output G for measuring skin conductance and providing a conductance output G related to the low-frequency conductance of and a set of three electrodes M, R, C for being positioned on the skin 3 of a body part of a subject. There are two common ways of attaching the electrodes to the skin. Either a special adhesive plaster or the contact gel itself could serve as the adhesive. These attachment methods and varieties of these will be well known for a person skilled in the art. M denotes a measuring electrode, R denotes a reference electrode, and C denotes a current carrying electrode. V denotes a constant voltage signal generator. The electrodes of the kit are supplied with electrolyte for providing electric contact between the electrodes M, R, C. Contacting surfaces between the electronic conductors of the electrodes M, R, C and the skin are, at least partially, provided by the electrolyte. The contacting surfaces comprise a contact electrolyte 4 having the property of not penetrating the sweat ducts when being positioned on the skin. The electronic processing unit drives a current electrode C from the signal generator V via the first op amp A. Thereby a periodic signal with a predetermined frequency set in the signal generator V is supplied to the electrodes C and an immittance measuring circuit B, R, X, LPF measures the resulting current and generates least a conductance signal based on the signal received from the measuring electrode M. The circuit works as an immittance measuring circuit in that the operational amplifier three electrode circuit imposes a voltage and reads a corresponding current. The predetermined frequency should be less than 30 Hz, for example 10 or 25 Hz, in order to reduce the contribution from the stratum corneum complex admittance.

The present invention is based upon measuring the increased admittance at low frequencies caused by sweat duct filling. As the stratum corneum SC and sweats ducts are essentially in parallel the admittance is proportional to sweat duct filling. Only the real part of the admittance (conductance) is used. By suppressing the contribution of the susceptance part, the effect of the capacitive contribution from stratum corneum wetting is made negligible.

An electrode contact area of, say 1 $cm^2$, means that a measurement covering some hundred sweat ducts is obtained. Statistically all these ducts are not completely filled simultaneously. After a sweat expulsion a sweat gland has a refractory period when it can not be reactivated. During that period a reabsorption process via the duct walls causes an active emptying process.

As previously described, the present invention is dependent on the use of a contact electrolyte or similar skin contact medium that does not interfere with the sweat activity, e.g. by filling up the ducts. On the other hand, some skin contact medium is required between the electrical conducting surface of the electrode and the skin to ensure good electrical contact and stabilise the measurement.

If the externally applied contact electrolyte fills or partly fills sweat ducts, the reabsorption process must be strong enough to empty the ducts of the contact electrolyte in a sufficiently short time. The efficiency of the re-absorption process can be characterised by a time constant of the monitored skin conductance signal over time, G(t), confer the falling parts 7 of the curve on FIG. 7. The reabsorption time constant can e.g. be calculated by fitting standard relaxation or decay curves to the falling parts of the curve on FIG. 7 to determine time constants. As an example, when using an exponential decay curve:

$$G(t)=G_i e^{t/\tau},$$

where $G_i$ is a constant and $\tau$ is the re-absorption time constant that can be determined by curve fitting algorithms. Alternatively, if G(t) is sampled at time a and b, the time constant $\tau$ is found from:

$$\tau=(b-a)/\ln(G(a)/G(b)).$$

A characteristic time constant is taken from the relaxation curve obtained with a test person undergoing a standardised routine, such as first being well relaxed (e.g. 15 min sitting in a chair), then doing physical exercise until the conductance is e.g. doubled, then relaxing again during which the relaxation curve is recorded and the time constant calculated as described.

Several commercial wet gel ECG electrode models have been tested but found to result in a more or less permanent filling of the sweat ducts corresponding to time constants of the order of 30 min or more, making them unsuitable for sweat activity measurements. Some solid gel ECG electrodes e.g. the Kendall/Arbo model H92SG have been found to have time constants of the order of 1 min or less and can be used in the present invention. The reabsorption time constant is also dependent on skin site and is specially short in palmar and plantar skin and long in forehead skin. A kit should therefore comprise a special purpose, optimized electrode type. Thus, depending on the time-span over which the monitoring runs as well as on the skin type at the used skin sites, different reabsorption time constants may be acceptable. In preferred embodiments, the reabsorption time constants of contact electrolyte from the sweat ducts into the Epidermis is therefore of less than 15 min. such as preferably less than 10 min.; 8 min.; 5 min.; 3 min.; or 2 min. The contact electrolyte giving the shortest time constant at a given skin site may be the best electrolyte for that site.

The present inventors envisage that one alternative to the solid gel electrodes can be the application of a dc current of correct polarity to wet gel electrodes, whereby a process of electro-osmosis may help to reduce the penetration of a contact electrolyte in the form of gels into the sweat ducts, however this remains to be tried. This however entails a more complex device than desired.

It is known that the dc potential of the measuring electrode is related to sweat activity; "Psychogalvanic reflex and changes in electrical parameters of dry skin" Grimnes et. al, Med Eng & Comp, 20, 1983, 734-740, hereby included as reference. The present inventors therefore also envisage that the DC voltage represents a useful parameter for e.g. multivariate analysis of measured data.

A measuring frequency below 60 Hz is used so that the stratum corneum ac conductance has negligible influence. Stratum corneum admittance contains an ac conductance component which is an error signal because it is related to sweat activity in an unpredictable way. Because it is frequency dependent the ac component of the stratum corneum can be reduced to an acceptable level by lowering the measuring frequency to 60 Hz or lower, such as 45 Hz or preferably 30 Hz or lower.

A three-electrode system has several advantages. It eliminates the need for a large neutral electrode. It also makes it possible to measure on two or more skin sites simultaneously. Sweat activity may vary between skin sites and with the present invention it is possible to use two common control electrodes plus only one electrode per measured skin site.

Referring again to FIG. 4 the lines through the skin tissue indicate electric current paths between the current electrode C and the measuring electrode M. The reference electrode R is without current flow. $Z_{sc}$ denotes the impedance of the stratum corneum and $Z_t$ denotes the impedance of the living, deeper layers of the skin. At low signal frequencies, e.g. 10 Hz, the impedance of the skin is largely dominated by the stratum corneum, so the impedance contribution of the underlying skin layers is negligible.

The potential between electrodes C and M is controlled by a first operational amplifier A which is connected to a signal generator V, e.g. an oscillator, on the positive input and to a reference electrode R on the negative input. Because of the high input resistance of the op amp A, there will be negligible current through the reference electrode, and op amp A will ensure that the impedance contribution from the current carrying electrode C is eliminated. In this manner the admittance measurement is restricted to the volume below the measuring electrode M. In addition, if there is a capacitive coupling of 50/60 Hz noise leakage current to the patient, the necessary ac current will be supplied by the C electrode, but will not disturb the current reading of the measuring electrode M.

The second operational amplifier B with a resistor R in the negative feedback loop serves as a current to voltage converter. The voltage is then multiplied in a multiplier X with the excitation sine wave signal from the signal generator V in order to extract the real part, the conductance, from the complex admittance. The multiplied signal is then low pass filtered LPF to obtain a dc value proportional to the conductance in the skin. This is basically a circuit similar to a lock-in amplifier.

Figure 5:
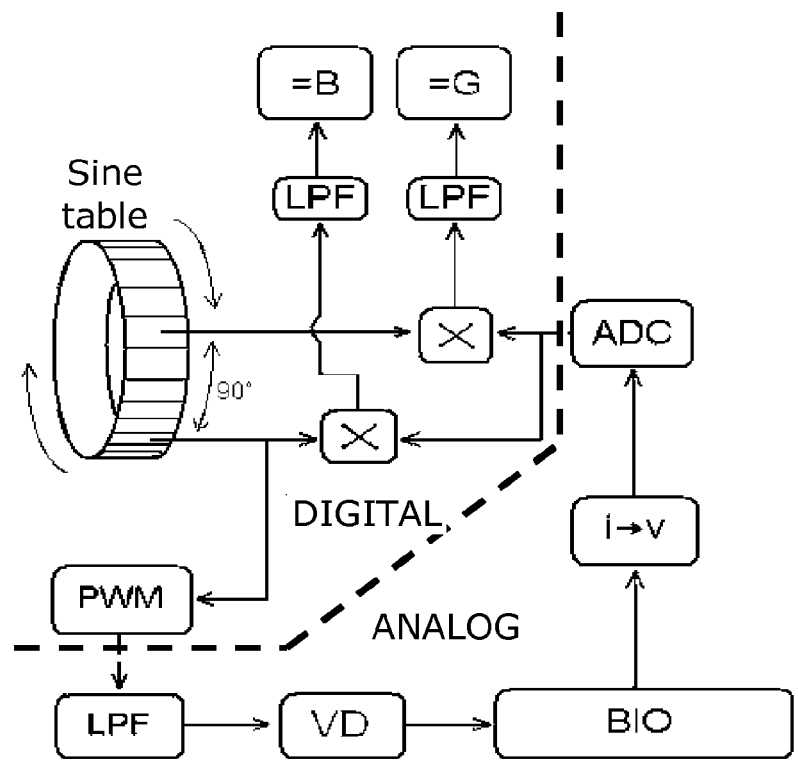
FIG. 5 illustrates a microcontroller based admittance measurement system according to the invention.

While FIG. 4 illustrates analogue circuit implementation of the electronic processing unit of the invention, FIG. 5 shows a second example embodiment of the kit according to the invention wherein some of the functions of the processing unit is performed in digital circuitry (DIGITAL) and some functions are performed in analogue circuitry (ANALOG), the two parts being indicated by the dotted line. The digital circuitry may comprise a microcontroller device, for example the PIC18F258 from Microchip™. A PIC18F258 microcontroller is an example of a microcontroller which is powerful enough to perform the required digital signal processing, and it also includes other desired features such as a PWM (Pulse Width Modulation) module, a hardware multiplier, a serial peripheral interface (SPI), a UART (Universal Asynchronous Receiver Transmitter) and ADC (Analogue-to-Digital Converter). A person skilled in the art will understand that microcontrollers or similar processors of other kinds may be equally suitable for use in the present invention.

In the digital circuit part the PWM module generates a sine voltage based on the input of values from a table of values for a sine function. The PWM duty cycle is controlled by values from the sine table being accessed by the program being executed in the microcontroller. By low pass filtering the PWM output, a sine voltage is then obtained. The PWM output is connected as an input to a voltage divider VD, whereby a suitable signal voltage amplitude may be generated for electrodes connected to the biological skin BIO to be measured. The need for separate oscillator circuitry is thus avoided. From the measuring electrode (not shown on the biological skin BIO a measured signal is converted from a current to a voltage I→V and input to an analogue→digital converter ADC. The output of the ADC is connected as an input to two mixers X, both being supplied with values from the sine table. The first mixer is supplied with the same values being supplied to the PWM-unit. When the output of this first mixer is passed through a low pass filter (LPF) an output representing the measured susceptance, B, is obtained. The second mixer is supplied with sine values representing a signal which is 90 degrees out of phase with the values supplied to the PWM-unit. Thus, when the output of this second mixer is low pass filtered LPF, a signal representing the conductance, G, is obtained.

The digitisation of the current reading voltage signal may be carried out by a Burr Brown ADS8341 analogue-to-digital converter ADC, which fulfils the requirements of a fast, high resolution converter with four channel multiplexing at a reasonable price. The digitized signal is transferred to the microcontroller by SPI (Serial Peripheral Interface) communication, as shown on FIG. 6. The microcontroller then performs the multiplication and digital low pass filtering in a process parallel to the signal sampling and sine generation. The selected microcontroller is a very efficient device in this application because it performs several tasks simultaneously. If required, it is also easy to obtain a value for the susceptance (B) of the admittance by multiplying with a sine which is minus 90 degrees out of phase from the excitation sine, as also shown on FIG. 5. Additional adjustment to the phase of the sine in the multiplication may be needed to compensate for phase shifts from the filters.

By using a suitable microcontroller in this way a kit according to the invention is provided which reduces the number of separate components to a minimum. The functions performed outside the microcontroller is limited to analogue filtering, voltage division, electrode system analogue circuitry, current to voltage conversion, signal amplification and analogue-to-digital conversion, as shown in FIG. 5.

Figure 6:
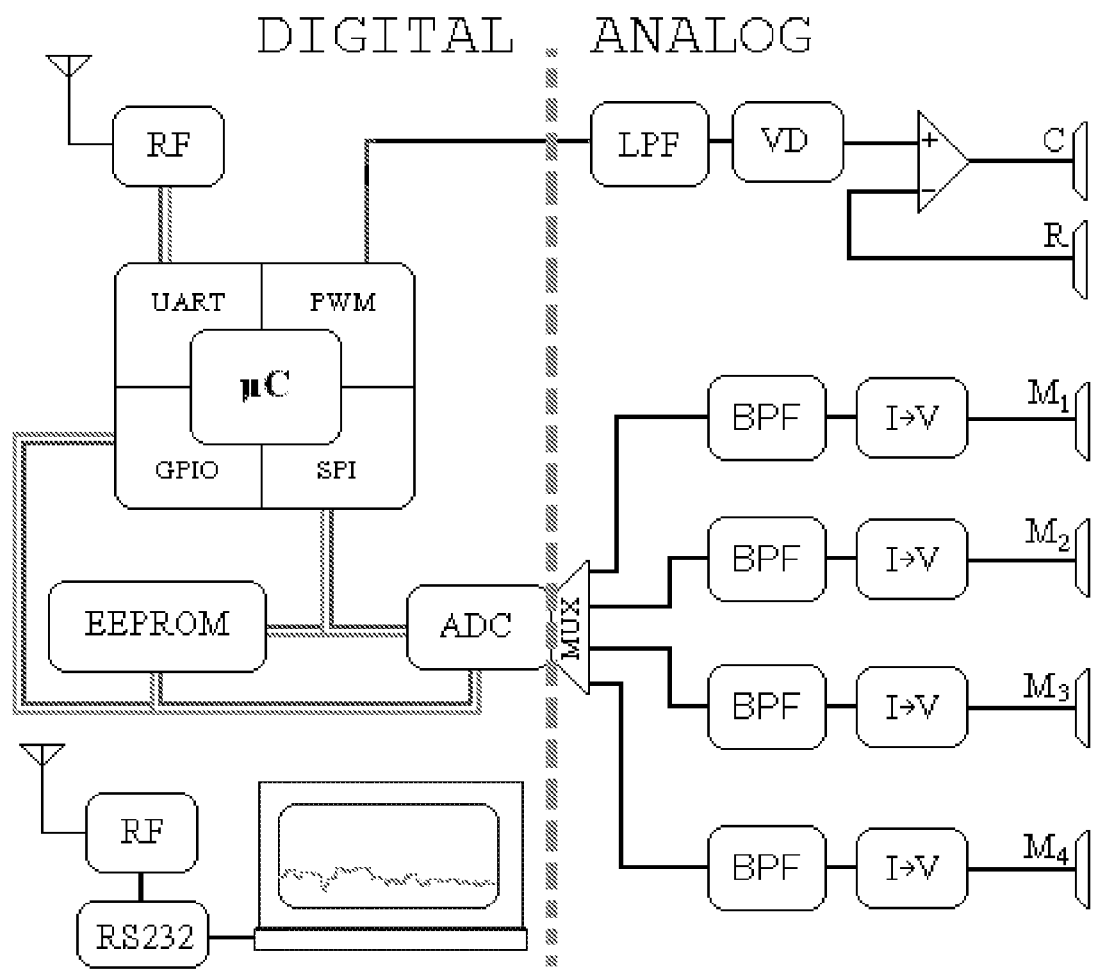
FIG. 6 illustrates the extension of the measurement principle to a multi-channel system, in this case a four-channel system where radiofrequency modules are used for wireless communication.

FIG. 6 also illustrates how the present invention may be extended to a multi-channel system, in this case a four-channel system. A radio frequency transmitter modules RF may be connected to a UART which in its turn is connected to or integrated with the microcontroller μC, for enabling wireless communication between the microcontroller μC with an external device, for example a Personal Computer PC arranged so close that a corresponding a receiving RF-module connected to the PC, for example via an RS232 interface, is able to receive signals transmitted from the RF-module of the processing unit connected to the skin electrodes $M_{1-4}$, R, C.

For the wireless solution the RC1280 transceiver module from Radiocraft may be used. Advantageously, this is very easy to implement in a microcontroller based system due to its embedded protocol. The module is small, cost-effective, has low current consumption and only requires one additional component, i.e. an antenna.

By using a multi-channel ADC having a multiplexer MUX on its input more channels (each channel connecting to a measuring electrode $M_N$, N=1, . . . , x; x being the total number of measuring electrodes) can be added to the system simply by including additional circuitry for each current-to-voltage conversion and band pass filtering (BPF) as shown in FIG. 6. A 32 kB EEPROM is connected to the microcontroller via the SPI bus local data storage in the device. Data will be continuously stored between each measurement as the device is powered on. With one measurement set per minute, four-channel data can be logged for more than two days before the memory runs out, with one measurement set per second more than one hour.

Figure 7:
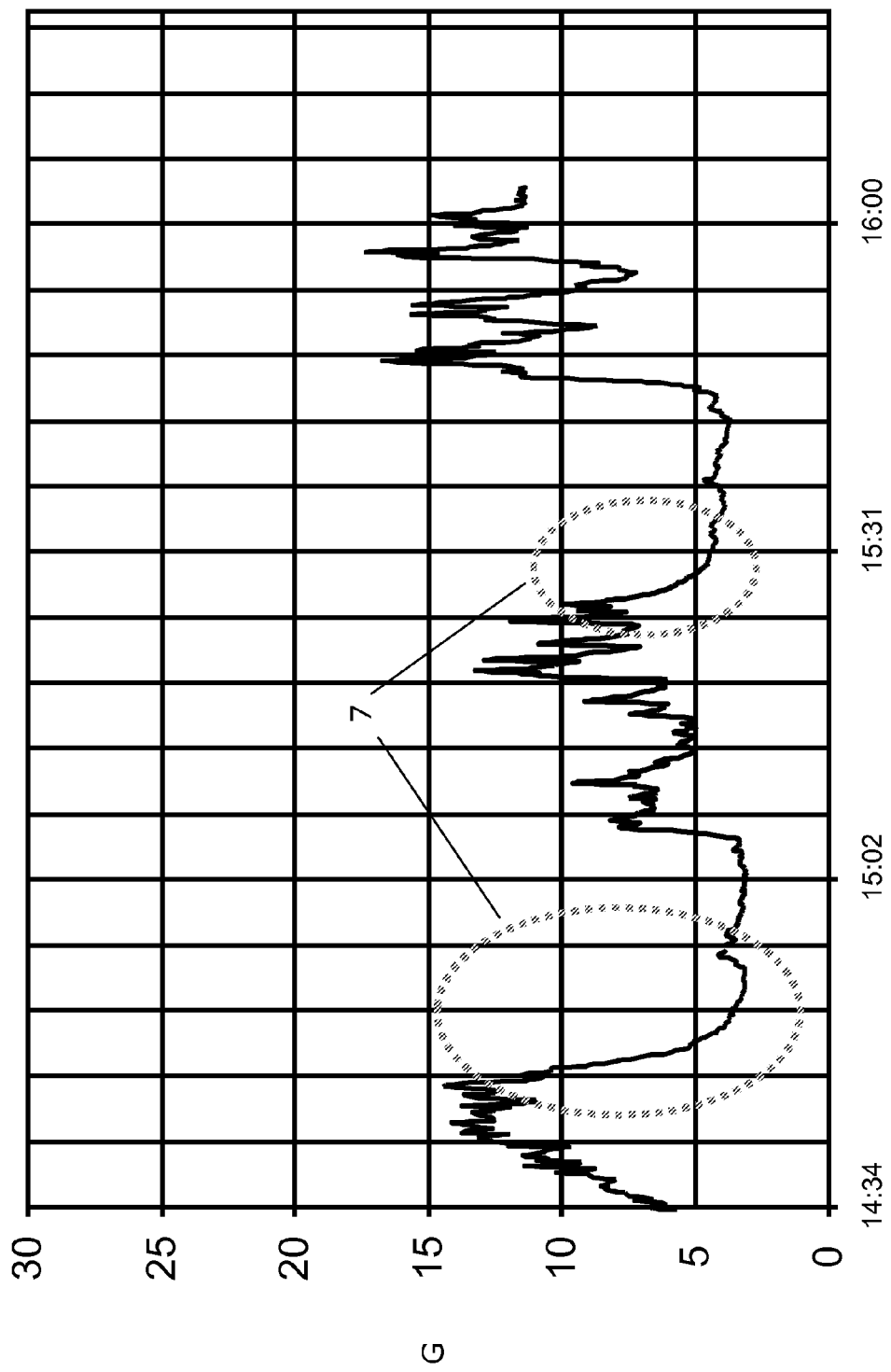
FIG. 7 illustrates a typical result over time of the conductance on the skin of a human, in this case on the thorax.

FIG. 7 shows an example of results that may be recorded with the present invention, and illustrates the measured skin conductance, G, as a function of time, t. The curve is a 1,5 hour recording obtained with a kit according to the invention when a set of electrodes is arranged on the thorax. The curve shows measurements during periods of rest, walking around and bicycling. More curves could have been obtained by using a four-channel device with sets of electrodes arranged on other positions on the body. The periods of walking around and bicycling on FIG. 7 are the periods characterised by fluctuations in the measured conductance, while the periods of rest are characterised by a falling curve following a period of activity or a near constant level when the subject has been at rest for some time.

The kit according to the invention may thus be used to obtain a measure of a physiological state of a subject by registering sweat activity and/or changes in sweat activity caused by the sympathetic nervous system. For this purpose the electronic processing unit comprises a sweat activity change estimation module. Such a change estimation module may be realised as part of the computer program running on the microcontroller and hence can be programmed to determine, by digital signal analysis, a coefficient of change in sweat activity versus time. In some embodiments of the kit according to the invention the program running on the microcontroller may be designed to identify fluctuations in the conductance signals and to use the identified level(s) of such fluctuations as measure of sweat activity. Such fluctuations may for example be identified using a frequency analysis module for performing frequency analysis of the conductance signal in order to identify an activity level of the subject based on the frequency content of the signals. In some embodiments of the invention such a frequency analysis of the registered sweat signal may be designed so as to identify an activity level, e.g. high activity or low activity, for the subject being monitored.

The physiological state obtained (sweat activity) is for some individuals closely related to the blood sugar level of the individual. Hence, in some embodiments of the invention there may be provided a blood sugar level estimator or warning device which uses the determined physiological state (sweat activity) to estimate a blood sugar level in the subject on whose skin the measurements are being obtained, and possibly to provide a warning signal in the event that an undesirable blood sugar level seems to be developing.

By arranging electrode sets on different parts of a subjects body the sweat activity is monitored for two or more different body parts of the subject. In this case the electronic processing unit of the kit is connected to corresponding two or more sets of electrodes, and each set of electrodes represents a separate monitoring channel. In some embodiment of the kit according to the invention the sweat activity is monitored over a period of time to determine a coefficient of change in sweat activity as a function of time.

Typically, the program which is installed and run on the microcontroller may also be equipped with a stratum corneum (SD) moisture content estimation module and a conductance correction module for correcting the conductance determined by the electronic processing unit using the determined moisture content, in order to determine a quantitative expression for the sweat activity.

When a kit according to the present invention is designed using a microcontroller a device small enough to fit in a pocket may be produced. Thus a kit has been provided in the form of a four-channel data-logger for constant voltage ac conductance (G) measurement in the stratum corneum layer of the human skin. The kit includes an oscillator circuit, electrode systems, current-to-voltage conversion, multiplicator circuitry and filtering. The microcontroller based device also has an Analogue-to-Digital Converter, an EEPROM (Electrically Erasable Programmable Read Only Memory) as a non-volatile memory for the digitisation and data storage.

The kit finds application in measurement of the degree of sweat activity in the skin. The kit may be applied for the clinical evaluation of the condition hidrosis which involves excessive sweat activity. The device also works well in EDR (Electro Dermal Response) ac measurements.

Fever is associated with periods of sweating. Thus, application areas for a simple and robust multiple channel sweat measuring system are therefore illness and fever, such as malaria, diabetes, and in general diagnostic activities correlating fever and sweating.

Other possible application areas of the invention are in neurology (sympaticus test, clinical autonomic disorders), physical training and exercise, early warning of thermal imbalance of the body (earlier than change in body core temperature, useful for military and diving activities, etc.), psychosomatic diagnosis, e.g. in the analysis of sleep disorders and stress (sweating before, under, and after a public performance), during menopause and analysing the effects of aging.

Another application area of the invention may be sweat measurements related to the electrodermal response (EDR). The present invention is believed to be better suited for EDR measurements than usual techniques.

Additional information about the sweating process and the membrane properties of the skin can, according to the well known Nernst concept, be obtained by adding measurements of the endogenous dc voltage. The endogenous dc voltage is the membrane potential developed by the semi-permeable skin membrane. This is made feasible with advanced electronic circuitry being able to separate the dc component from the ac component on one or more channels. A dc measurement means that the dc potentials are recorded simultaneously with the ac measurements. The endogenous dc voltage is related to skin properties as a semi-permeable membrane and hence also to sweat activity. Realising this, it will be understood that measurement of the endogenous dc voltage may in some embodiments of the invention provide data which when combined with the other results obtained with this invention, as detailed above, enhance the results of the present invention.

Because the present invention utilizes a contact gel which do not penetrate into the sweat ducts in any way similar to ordinary commonly used electrolyte contact gels, the present invention may also provide improved sensitivity in EDR (Electro-Dermal Response) measurements. EDR is found in particular on palmar and plantar skin areas, but during sweating synchronous waves may be found on other skin areas as well. EDR is due to a sudden outbreak of sweat activity, which the present invention is well suited to registering. The EDR waves are typically relatively slow waves with maximum delay and rise time of about five seconds and a longer fall time. Knowing these typical parameters, a person skilled in the art may design a signal frequency analysis aimed at detection of EDR waves. This could for example be realised as part of a digital signal analysis being executed on the microcontroller. Alternatively, conductance data obtained using the present invention could be analysed in an external computing device, such as a personal computer (PC) after conductance measurement data have been transferred to the computing device.

The present invention may be effectively utilized in the doctor's office, in the clinic and at home. This is achieved by a combination of a wireless data transfer when the kit and the PC are within contact range, and an internal memory device inside the kit has stored data which can be harvested after a measurement session.

Cited References
U.S. Pat. No. 5,738,107
EP 0 315 854 A1
WO 92/06634
JP 2005052227 A
JP 07303618 A
"An instrument for the evaluation of skin hydration by electrical admittance measurement", Ø. G. Martinsen & al, in Innov. Tech Biol. Med., Vol. 14, No. 5, 1993, p. 589-596
"Continuous estimation of parameters in skin electrical admittance from simultaneous measurements at two frequencies", L. Mørkrid and Z.-G. Qiao, in Medical & Biological Engineering & Computing, November 1988, pp. 633-640
"Continuous monitoring of sweating by electrical conductivity measurement" A. K. M. Shamsuddin and T. Togawa, in Physiol. Meas., Vol 19, 1998, pp 375-382
"Psychogalvanic reflex and changes in electrical parameters of dry skin" Grimnes et. al, Med Eng & Comp, 20, 1983, 734-740

The invention claimed is:

1. A kit for monitoring sweat activity, comprising:
an electronic processing unit for measuring a conductance signal; and
a set of three electrodes to be positioned on skin sites of a subject,
wherein the electronic processing unit comprises an electrode drive circuit for applying a periodic signal with a predetermined frequency of less than 60 Hz to at least one of the electrodes to reduce the contribution from the stratum corneum complex admittance, and an immittance measuring circuit for measuring at least a conductance signal received from at least one of the electrodes, and
wherein the electronic processing unit is configured to identify fluctuations in the conductance signals and to use a level of such fluctuations as a measure of sweat activity.

2. The kit according to claim 1, wherein the electronic processing unit comprises a sweat activity change estimation module configured to determine, by signal analysis, a coefficient of change in sweat activity versus time.

3. The kit according to claim 1, wherein the electronic processing unit comprises a frequency analysis module for performing frequency analysis of the conductance signal in order identify an activity level of the subject based on the frequency content of the signals.

4. The kit according to claim 1, wherein the electronic processing unit also uses the DC voltage component generated by the skin under the measuring electrode.

5. The kit according to claim 1, wherein the electronic processing unit comprises a stratum corneum moisture content estimation module for measuring moisture content in the stratum corneum and a conductance correction module for correcting the conductance corresponding to the moisture content measurement.

6. The kit according to claim 1, further comprising a contact electrolyte supplied on or to be supplied on the electrodes, which electrolyte does not substantially fill the sweat ducts when positioned on the skin and/or has a re-absorption time constant from the sweat ducts into the epidermis of less than 15 minutes.

7. A method for determining a physiological state of a subject by registering sweat activity caused by the sympathetic nervous system, the method comprising:
applying a kit to a subject, wherein the kit comprises:
an electronic processing unit for measuring a conductance signal and a set of three electrodes to be positioned on skin sites of the subject,
wherein the electronic processing unit comprises an electrode drive circuit for applying a periodic signal with a predetermined frequency of less than 60 Hz to at least one of the electrodes to reduce the contribution from the stratum corneum complex admittance, and an immittance measuring circuit for measuring at least a conductance signal received from at least one of the electrodes, and
wherein the electronic processing unit is configured to identify fluctuations in the conductance signals and to use a level of such fluctuations as a measure of sweat activity; and
monitoring sweat activity of the subject using the kit.

8. The method according to claim 7, wherein the physiological state is related to blood sugar.

9. The method according to claim 7, wherein sweat activity is monitored for two or more different skin sites of the subject and for which the electronic processing unit of the kit is connected to corresponding two or more sets of electrodes, and wherein each set of electrodes represents a separate monitoring channel.

10. The method according to claim 7, wherein the sweat activity is monitored over a period of time to determine a coefficient of change in sweat activity as a function of time.

11. The method according to claim 7, comprising a frequency analysis of the registered sweat signal in order to identify an activity level, e.g. high activity or low activity, for the subject being monitored.

12. The method according to claim 7, further comprising:
    determining a moisture content in the stratum corneum; and
    correcting the conductance corresponding to the moisture content to determine a quantitative expression for the sweat activity.

13. The method according to claim 7, further comprising measuring endogenous dc voltage.

14. A method for monitoring sweat activity of a subject over time, the method comprising:
    providing an electronic processing unit for measuring a conductance signal via a set of three electrodes to be positioned on skin sites of a subject;
    arranging the electrodes in electric contact with the skin via a contact electrolyte, wherein the contract electrolyte does not substantially fill the sweat ducts when positioned on the skin or has a re-absorption time constant from the sweat ducts into the epidermis of less than 15 minutes;
    applying a periodic signal with a predetermined frequency of less than 60 Hz to the electrodes to reduce the contribution from the stratum corneum complex admittance;
    measuring at least a conductance signal received from the electrodes; and
    identifying fluctuations in the conductance signals and using a level of such fluctuations as a measure of sweat activity.

15. The method according to claim 14, wherein the contact electrolyte is an electrically conductive solid gel.

* * * * *